United States Patent
Gardner

(10) Patent No.: US 7,812,960 B2
(45) Date of Patent: Oct. 12, 2010

(54) OPTICAL ULTRASOUND DEVICE

(76) Inventor: Judd Gardner, 7575 Linda Vista Rd., Apartment 48, San Diego, CA (US) 92111

(*) Notice: Subject to any disclaimer, the term of this patent is extended or adjusted under 35 U.S.C. 154(b) by 408 days.

(21) Appl. No.: 11/873,323

(22) Filed: Oct. 16, 2007

(65) Prior Publication Data
US 2009/0097012 A1 Apr. 16, 2009

(51) Int. Cl.
*G01B 9/02* (2006.01)
(52) U.S. Cl. .................................... 356/477
(58) Field of Classification Search ............... 356/477, 356/483, 35.5, 478, 481, 482
See application file for complete search history.

(56) References Cited

U.S. PATENT DOCUMENTS

| | | | |
|---|---|---|---|
| 5,091,983 A * | 2/1992 | Lukosz | 385/13 |
| 5,448,058 A | 9/1995 | Arab-Sadeghabadi | |
| 6,200,266 B1 | 3/2001 | Shokrollahi | |
| 6,208,590 B1 | 3/2001 | Kim | |
| 6,314,056 B1 | 11/2001 | Bunn | |
| 6,496,264 B1 | 12/2002 | Goldner | |
| 6,728,165 B1 | 4/2004 | Roscigno | |
| 7,245,789 B2 | 7/2007 | Bates | |
| 2005/0002628 A1 | 1/2005 | Rahman | |
| 2005/0157305 A1 | 7/2005 | Yu | |

OTHER PUBLICATIONS

De Lima, Beck, Hey, Santos, Compact Mach-Zehnder acousto-optic Modulator, Applied Physics Letters, 2006, vol. 89, 121104, American Institute of Physics, USA.

Lemaitre-Auger, Acoustic-optic intensity modulation on glass integrated optic, Integrated Optics:Devices, Materials, and Tech. VIII, Proc. of SPIE, 2004, vol. 5355, 120, USA.

Schott North America, Inc., Technical Information: Optics for Devices, TIE-27: Stress in Optical Glass, Jul. 2004, Schott North America, USA.

W. P. Mason, Physical Acoustics and the Properties of Solids. D. Van Nostrand Company, Princeton, New Jersey. 1958.

M. G. Silk, Utrasonic Transducers for Nondestructive Testing, Adam Hilger Ltd., Bristol, OK, 1984.

Thomas L. Szabo, Diagnostic Ultrasound Imaging: Inside Out, Elsevier Academic Press, San Diego, CA, 2004.

* cited by examiner

*Primary Examiner*—Hwa S. A Lee
(74) *Attorney, Agent, or Firm*—Mark Wisnosky

(57) ABSTRACT

A new optical ultrasonic analysis transducer is described. The device includes a new detection means for the reflected ultrasound signal. The detector may be incorporated into a microchip design. The detector is compatible with a variety of material and design geometries that may be optimized for the particular application. Versions of the device may optionally include both excitation and receiving elements on the same device or these elements may be separate. Example designs are shown with applications to continuous wave ultrasound analysis useful for example in Doppler fluid flow measurements. Other designs are shown with multiple arrays and multiple excitation transducers to allow flexible three-dimensional imaging apparatus to be built. An equivalent circuit analysis of the frequency response and signal sensitivity provides means to customize material selection and other design parameters for particular applications.

19 Claims, 16 Drawing Sheets

OPTICAL ULTRASOUND DEVICE

TECHNICAL FIELD

Embodiments of the invention relate to an ultrasound device whose design may be modified so that it may be used in wide variety of ultrasonic imaging applications such as medical imaging and material testing purposes.

BACKGROUND OF THE INVENTION

Ultrasound imaging has been in wide use in a variety of industries. In the typical application, a piezoelectric element is used for both excitation and detection of the ultrasound signal. In a noninvasive use, such as the medical application of prenatal imaging, a piezoelectric element is placed in intimate contact with the pregnant woman's body to be tested and the element is excited with an electrical pulse with a center frequency selected for optimum penetration to the area of interest. The images allow assessment of the condition of the developing fetus. Arrays of sensors are often used to simplify data acquisition, improve spatial resolution, and improve signal to noise. Such arrays may also allow creation of a structured ultrasound beam that may be steered and provide for three-dimensional imaging applications.

Cannula and laproscopic medical applications of ultrasound imaging place greater restraints on the size of the excitation and sensing elements. Structures where the excitation and sensing elements are integrated onto a single substrate are required. Designs using a continuous sinusoidal excitation may make use of the Doppler frequency shift of the reflected signal to measure flow velocities. One disadvantage of such designs is that the electrical signal required for excitation of the piezoelectric device is generally several orders of magnitude larger than the electrically measured reflected signal using a piezoelectric detector. The designs therefore require high excitation voltages and low signal voltages on the same micro device. Interference requires careful design considerations for isolation of signals. Additionally, signal to noise often limits the applicability of the device. In many cases, the proper operation of piezoelectric devices is precluded by electrical noise.

The depth to which a sample may be probed is dependent upon the sample's material composition, the frequency of the ultrasound device and the sensitivity of the detector. Designs are required that will allow a variety of materials to be incorporated into the sensing element for optimum operation over a wide range of frequencies. Designs are most often unique to the application. Even in a single application, the sensor design might vary dependent upon the material. In a medical imaging scenario, the density, and therefore response of bone material, is significantly different from muscle, fat or fluids. Designs are required that can image all such materials.

The integration of optical sensors into an ultrasound system is known. Optical sensors incorporating a Mach-Zehnder interferometer are used in oil and gas exploration and in underwater applications. These designs are composed primarily of two optical fibers that equally split the light from a single source.

The interferometer makes use of the change of the refractive index in one of the glass optical fibers when it is placed under mechanical stress during detection of an acoustic signal, and when the light from the two optical fibers is recombined. Due to the mechanical stress applied along one arm of the interferometer and the resultant induced refractive index change, a phase difference between the light of the two paths in the interferometer is generated that is proportional to the acoustic signal. In these applications, the size of the probe is often not a concern and very long sensors, often several meters, are used for increased sensitivity. Another advantage of such probes is that the sensor electronics may be located remotely from the sensor. The sensor that is in contact with the sample consists only of optical fiber. The sensor may therefore be used in corrosive or otherwise dangerous environments. Additionally, since this is an optical sensor, it would not be affected by intrinsic or extrinsic electromagnetic interference, or noise inherent in the materials of typical sensors.

Each of the designs and applications make use of particular features of an ultrasound detector. There is, however, no single design that can incorporate the multiple advantages. There is a need for a small fully integrated ultrasound detector that can operate over a wide frequency range and that can be configured for a variety of applications. There is a need for a detector that can operate in both a continuous and a pulsed mode and that can be fabricated either as a single element or as an array of elements. There is a need for an ultrasound detector that eliminates the requirement to isolate the high voltages of an excitation piezoelectric device from the low level reflected signal. There is a need for an ultrasound device design that can operate in a variety of environments. There is a need for an ultrasound detector device that can be used for imaging applications, create structure beams for three dimensional imaging, and also be used for Doppler measurements. There is a need for an ultrasound device that can place the processing electronics either remotely from the sensor device or locally to the sensor device. There is a need for an ultrasound detector device that can incorporate excitation and detection on a single substrate but that can also be designed with excitation remote from detection.

SUMMARY OF THE INVENTION

An ultrasound detector based upon optical interferometry is described. The detector provides advantages of sensitivity, noise immunity and compact design. The device may be designed as an optically isolated sensor with all electronics located remotely from the point of measurement. In another embodiment the device is designed with all electronics incorporated on the same substrate as the sensor. The device may be used in a variety of modes. In one embodiment the device is a single element sensor composed of a piezoelectric transmit and receive element located on a single substrate. The same piezoelectric element is used as the acoustical signal receiver for the reflected pulse. Timing of the excitation and detection circuits is used to detect single pulse excitation. The fact that the device uses optical detection of the reflected pulse minimizes electronic interference from the excitation pulse and any other potential electromagnetic interference. In another configuration, a piezoelectric excitation element and a separate acoustical signal-receiving element are located on the same substrate. The device so configured may be operated in a continuous excitation and receiving mode. Acoustical sensors are often operated in an array to improve signal to noise and provide higher spatial resolution images. With multiple excitation sources and a structured excitation beam, acoustical sensors may provide three-dimensional imaging. The compact design of the invented sensors helps to facilitate multiple sensor imaging applications. The optical sensing avoids electrical cross talk amongst the multiple sensors when so used as well as electrical interference from any other electronic devices operating in the neighborhood of the testing. In another embodiment, multiple piezoelectric elements are located on the same substrate. Multiple piezoelectric elements may act both for excitation and for receiving the reflected acoustic signals. In one embodiment, multiple elements share the same optical interferometer detection device. The signal from individual sensor elements is sorted by timing sequences. In another embodiment, multiple individual optical sensors may be located on the same substrate. Dynamic steering of the excitation beam and dynamic focusing is enabled in this configuration.

DETAILED DESCRIPTION

Description of the Devices

Detailed embodiments are described referring to the attached figures. The exemplary descriptions demonstrate the flexibility of the invented design. All possible combinations of the features described are not necessarily included but will be apparent to those skilled in the art. For example, separation of the excitation and detection components is possible with all of the devices, not just those where the feature is explicitly described. Other features likewise may be shared amongst the various designs. The detailed descriptions of the selected examples are in no way intended to limit the other possible combinations of features.

Figure 1:
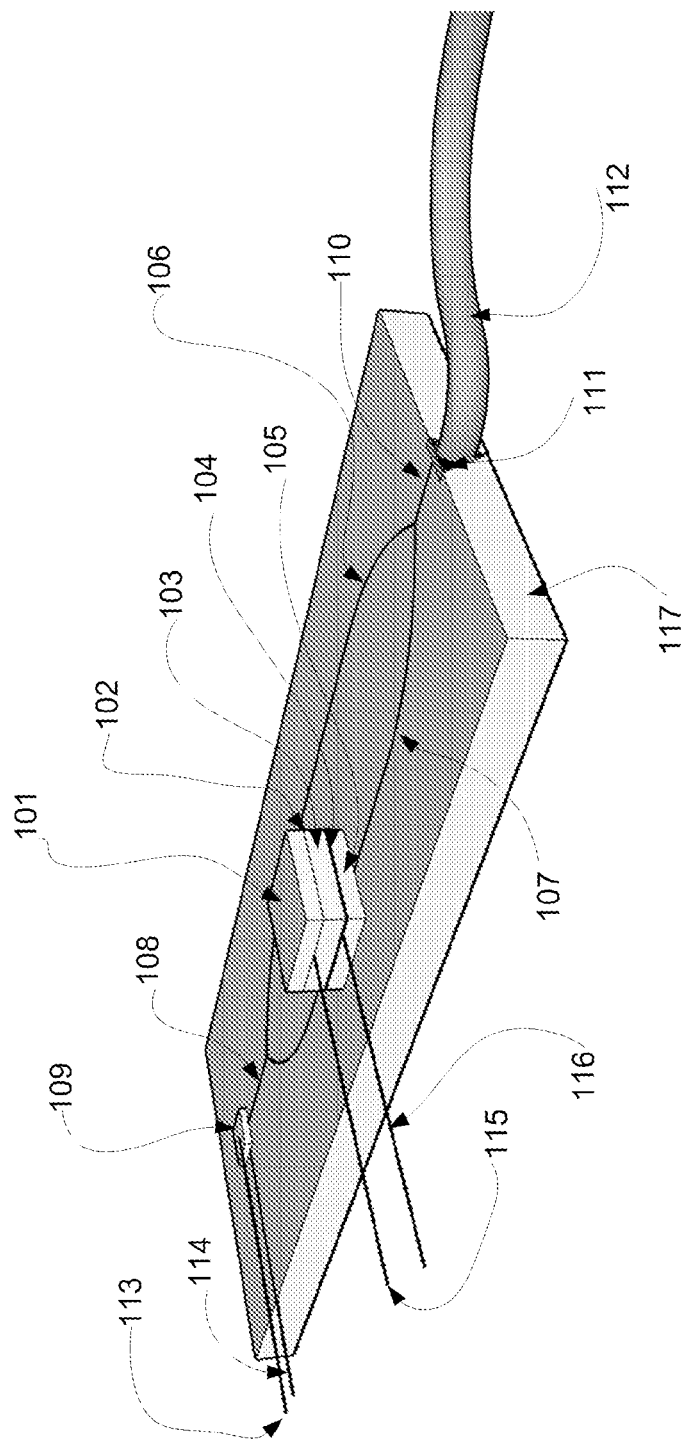
FIG. 1 is a schematic representation of a single element excitation and receiving element device.

A single element transducer shown in FIG. 1 exhibits a stack composed of a matching layer 101, a top electrode 102, a piezoelectric element 103, a bottom electrode 104, and a backing layer 105. The stack is mounted on the top surface of the substrate 117 symmetrically over the modulated arm of a Mach-Zehnder interferometer 107. The medium under test, not shown, is intimately attached to the matching layer 101.

The material of the matching layer is selected to provide good acoustical coupling between the material under test and the sensing device. In one embodiment to maximize the coupling between the modulated arm of the interferometer 107 and the stack 101, 102, 103, 104, 105, the wave-guides of the interferometer are formed by ion diffusion so that the interferometer wave-guide channels are flush with the substrate surface and therefore are in close proximity to the stack. In a preferred embodiment, the single element transducer is used in pulsed mode. A short electronic voltage excitation pulse is delivered across the piezoelectric element by the wires 115, 116 and the top 102 and bottom 104 electrodes. The short excitation pulse temporarily deforms the piezoelectric element 103 in the direction normal to the stack. Following the cessation of the excitation pulse, the piezoelectric element attempts to return to its original state. Due to the chosen stack and substrate material characteristics and dimensions however, the piezoelectric element mechanically oscillates in a heavily damped manner so that only a short oscillation is emitted through the matching layer 101 into the medium under test. The fundamental frequency of the emitted oscillation is largely dependent on the thickness of the piezoelectric element. The optical portion of the device is composed of the laser diode 109 with two attached wires for power 113, 114, the two arms 106, 107 of the interferometer diffused into the substrate 117, the entrance 108 and exit 110 wave-guides, the optical fiber output 112, and the V-groove coupling structure 111. Without a signal in the stack 101-105, the interferometer is in steady state. In a preferred embodiment, the length of one interferometer arm is longer than the other by one-quarter wavelength with respect to the wavelength of the laser diode 109 output. In order to operate the device, an appropriate signal is applied to the electrodes 115, 116 of the piezoelectric element to cause a short ultrasound pulse to be transmitted from the piezoelectric element 103 through the coupling layer 101 into the material under test, not shown. The reflected waves that travel back to the stack 101-105 cause the stack to vibrate. Due to the mechanical coupling between the stack and the substrate that is situated in the vicinity of one of the arms of the interferometer, the index of refraction in the one arm 107 of the interferometer changes in accordance with the received signal vibration. The change in the index of refraction causes a related phase shift in the light propagating through the one arm of the interferometer 107. The optical interference caused by the combination of the light propagating in the one arm 107 of the interferometer with the unchanged light propagating through the other arm 106 of the interferometer results in an optical signal that relates to the signal vibration received by the stack. Since the signals of interest are wideband, a wideband transmit and receive mechanical structure is required. The optical fiber 112 is connected to remote photo sensing and signal processing electronics, not shown.

In another embodiment, the backing layer material 105 is selected to provide damping of the excitation pulse. In another embodiment, not shown, the backing layer 105 is not required. In a preferred embodiment, the substrate is made of soda lime glass. In a preferred embodiment, the interferometer 108, 106, 107, 110 is prepared by techniques known in the art for patterned diffusion of material into the substrate 117. The diffusion process results in areas of higher refractive index that serve to form the optical channels 106, 107, 108, 110.

In another embodiment, the substrate may be made of other materials non-limiting examples of which include multi-component glasses, $SiO_xN_y$:$SiO2$:$Si$, $TiO_2/SiO_2/Si$, Lithium Niobate, III-V compounds such as InP or GaAs, and various polymers such as polyethylene terephthalate, polyethylene naphthalate, and polyimides such as poly(4,4'-oxydiphenylene-pyromellitimide) sold by DuPont® under the name Kapton®. Fabrication techniques are known in the art to create the required wave-guides in each of these various types of substrate. Embodiments using various glasses may use the ion exchange techniques to create channels of higher refractive index within the glass substrate. Embodiments using $SiO_xN_y$:SiO2:Si, $TiO_2$/$SiO_2$/Si may use thermal oxidation, chemical vapor deposition, flame hydrolysis deposition, sol-gel and other techniques for creating the wave-guides. Embodiments using Lithium Niobate may use metallic diffusion or protonic exchange to create the wave-guides electron cyclotron resonance. Embodiments using III-V compounds such as InP or GaAs may use various epitaxy techniques such as molecular beam epitaxy, liquid phase epitaxy, chemical vapor deposition and metal-organic chemical vapor deposition to form the wave-guides. Embodiments using polymeric substrates may use spin coating and dip coating techniques to form wave-guides. The variations in substrate materials may be included in the above and the following exemplary variations in structure.

Figure 2:
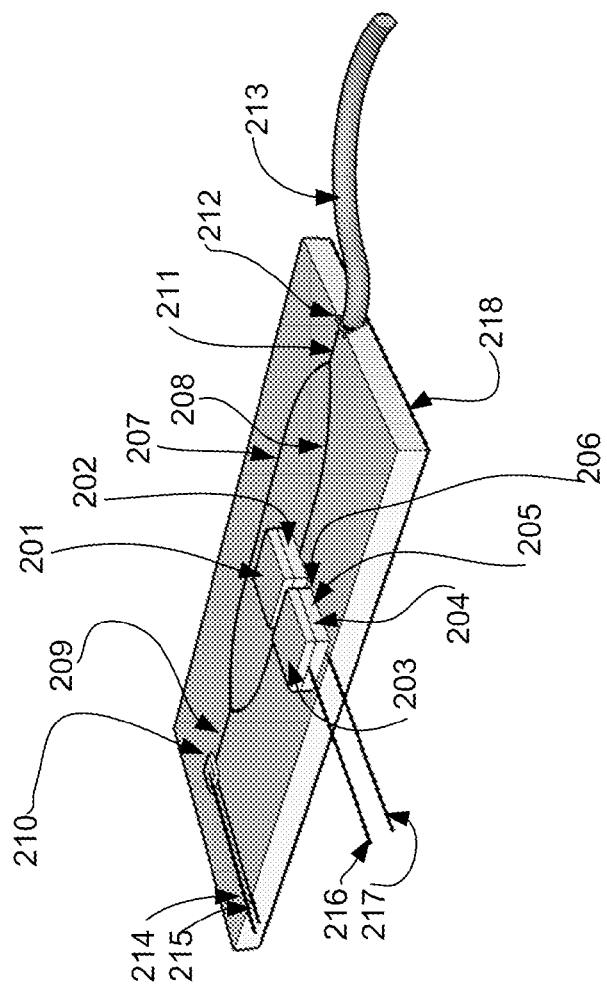
FIG. 2 is a schematic representation of a device having separate excitation and receiving elements.

In another embodiment shown in FIG. 2, the sensing stack 201, 202 is separate from the piezoelectric excitation stack 203, 204, 205, 206. The embodiment enables a continuous wave Doppler measurement. The transmit stack is composed of a matching layer 203, a top electrode 204, a piezoelectric element 205, and a bottom electrode 206. The receiving stack is comprised of a matching layer 201 and an appropriately chosen block of material 202 designed to optimize the receive function. The receive stack is shown to be mounted on the top surface of the substrate 218 symmetrically over the modulated arm 208 of the interferometer. In a preferred embodiment, the wave-guides 207, 208, 209, 211 of the interferometer is formed by diffusion. The resultant flat surface maximizes the coupling between the modulated arm of the interferometer 208 and the receive stack 201, 202. In a preferred embodiment, the device of FIG. 2 is operated as a continuous wave Doppler transducer. An electronic sinusoidal voltage excitation signal is delivered across the piezoelectric element of the transmit stack by the wires 216, 217. The excitation signal deforms the piezoelectric element in a sinusoidal manner with direction normal to the stack 203, 204, 205, 206. The resonant frequency is determined by the material characteristics and dimensions of the transmit stack and substrate. The piezoelectric element 205 mechanically oscillates in a continuous sinusoidal mode so that a continuous sinusoidal oscillation is emitted through the coupling layer 203 into the medium under test, not shown. The thickness of the piezoelectric element is chosen in accordance with the frequency of the sinusoidal excitation signal in order to optimize the signal that is emitted into the medium under test. In a preferred embodiment, the excitation stack 203-206 omits the backing layer 105 of the FIG. 1 example. The reflected signal from the object under test will fall within a narrow frequency band around the excitation frequency. In a preferred embodiment to enhance sensitivity, the materials and dimensions of the receiving stack 201, 202 and the substrate 218 are selected such that there is a mechanical resonance at the excitation frequency. The remaining elements of the embodiment shown in FIG. 2 function as those of the FIG. 1 example. Power is supplied to laser diode 210 through power leads 214, 215. The light from the laser diode enters the wave-guide 209 and is split to follow the two arms of the interferometer 207, 208. The light from the two paths is recombined in a wave-guide 211 that is coupled through a V-groove coupling structure 212 to an exit optical fiber 213.

The other end of the optical fiber 213 is connected to the optical detection and signal analysis electronics, not shown.

Figure 3:
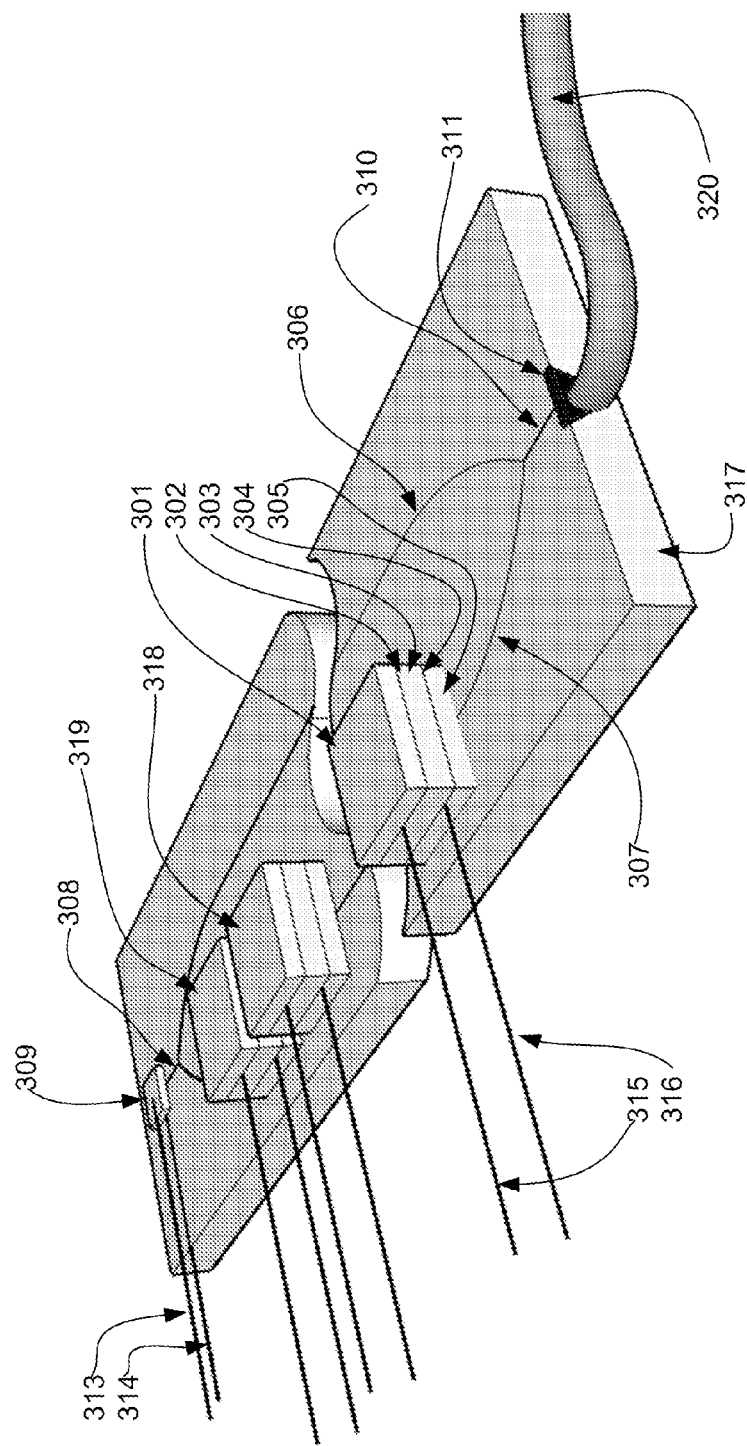
FIG. 3 is a schematic representation of a multiple excitation and receiving configuration.

A multiple sensor embodiment is shown in FIG. 3. Similar to previously discussed embodiments, the excitation piezoelectric and detection are in a stack consisting of a matching layer 301, a top electrode 302 and piezoelectric crystal 303 and bottom electrode 304 and a backing layer 305. Power is supplied to the piezoelectric crystal for excitation through leads 315, 316. The optical components of the sensor again include a laser diode 309, which receives power through leads 314, 315. The laser diode is coupled to a wave-guide 308 that splits to form the two arms of a Mach-Zehnder interferometer 306, 307. The two beams are recombined in the exit wave-guide 310, which is coupled to an optical fiber 320 through a V-groove coupling structure 311. In a preferred embodiment, the wave-guides are created through a diffusion process into the substrate 317. The end of the optical fiber 320 is coupled to the optical detection and signal processing electronics, not shown. A plurality of stacks of which just three are shown in the figure: 318, 319, and elements 301-305, are included in the same substrate. The plurality of excitation and detection stacks with the shared Mach-Zehnder interferometer enable operation in a B-scan mode as is known in the technology. The multiple stack configurations may be operated in a variety of modes, some standard and some likely not yet discovered. Variations in the timing, operating frequency, detection and analysis and physical configuration provide a hardware device with flexibility in operation modes that have yet to be explored by practitioners. Although shown as a linear array, other embodiments include circular and additional placement geometries. In another embodiment not shown, the excitation and detection stacks may be separated similarly to that shown and discussed in FIG. 2 above. In other embodiments with separate excitation and detection elements, there may be excitation elements that are greater or fewer in number than the detection elements.

Figure 4:
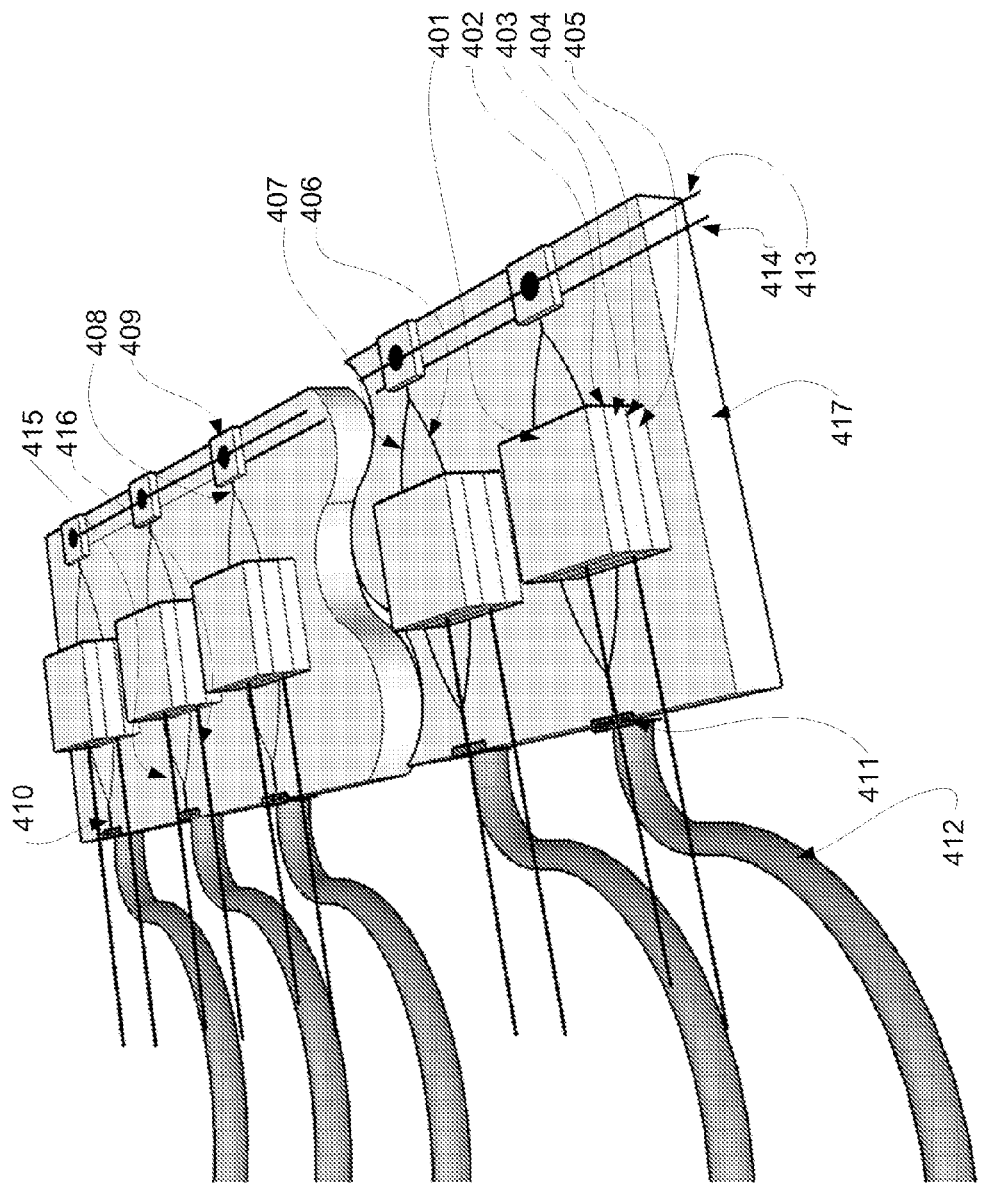
FIG. 4 is a schematic representation of a multiple independently operable excitation and receiving element configuration.

Another embodiment of the invention shown in FIG. 4 allows complete independent operation of each excitation and sensor stack within an array located on a single substrate. Each stack is comprised of a matching layer 401, upper 402 and lower 404 electrodes of a piezo element 403, and a backing layer 405. Five such stacks each with the same element set 401-405 are shown in the figure. In another embodiment, the stacks are disposed in configurations other than a linear configuration. The configuration is chosen to optimize imaging of the particular specimen to be analyzed. Each of the multiple stacks is positioned over a single arm of a single Mach-Zehnder interferometer 406, 407. Light for the multiple interferometers is supplied by individual laser diodes 409 within an array excited through connections 413, 414. Light from the laser diode follows channels 408 and is split into the arms of the interferometer 406, 407. Light from the interferometer is recombined in a channel 410 and connected through a V-groove 411 to an optical fiber 412. The end of the optical fiber 412 is connected to the signal processing electronics, not shown. The physical configuration and the multiple stacks of the embodiment shown in FIG. 4 enable a variety of operation schemes. The piezo elements 403 in each stack may be operated singly with multiple element detection by all stacks in the array. In another embodiment, a set of the multiple piezo elements are operated simultaneously to provide a steerable excitation beam with multiple location detection by multiple sensor stacks. In another embodiment, not shown, aspects of both the FIG. 2 and FIG. 4 are combined. The multiple stacks of FIG. 4 may be split into separate excitation 203-205 and detection 201, 202 stacks as shown in FIG. 2. Such a configuration enables continuous or pulse wave excitation, a steerable and focusable excitation beam obtained from multiple excitation elements that allows for three dimensional imaging, increased sensitivity and design simplification as would be familiar to one skilled in the art.

Figure 5:
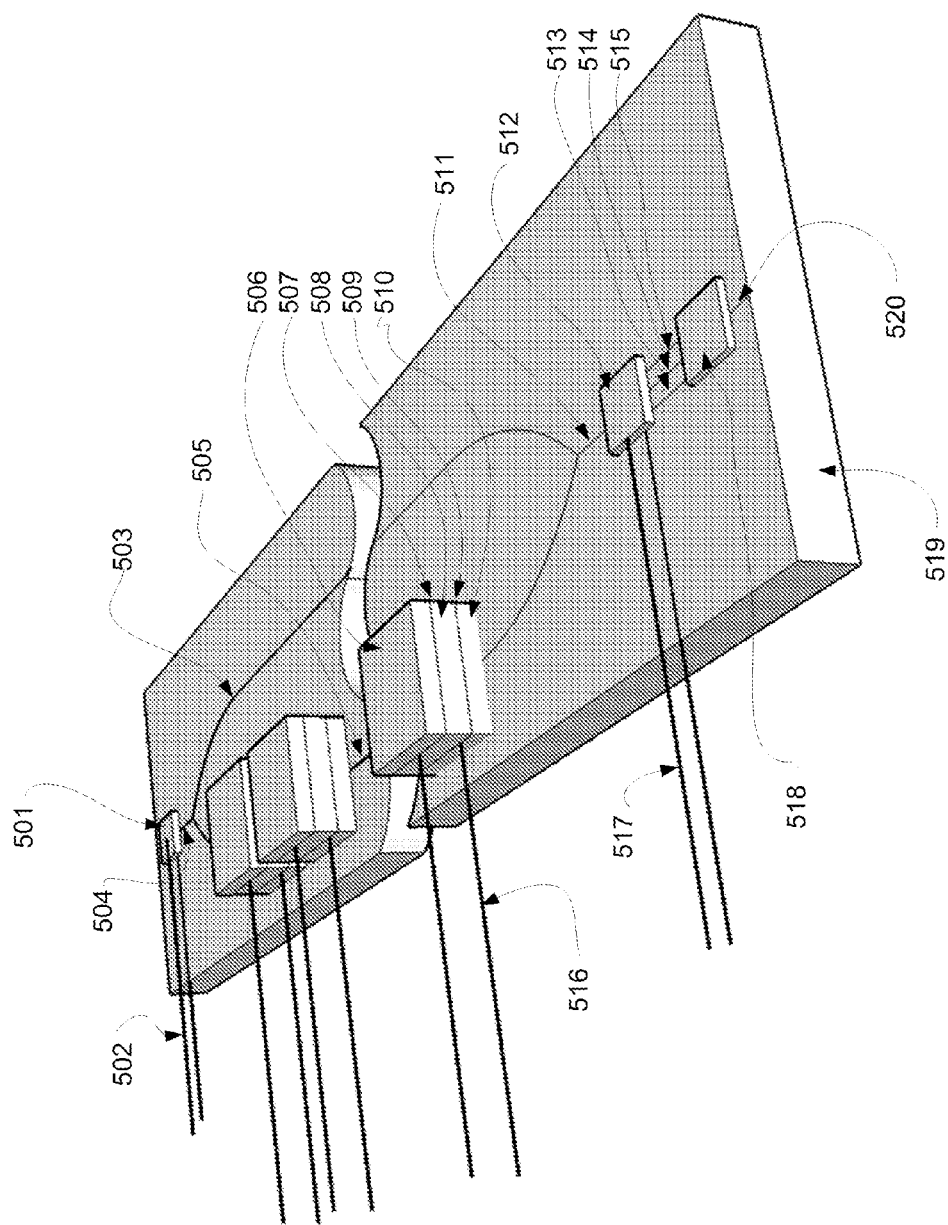
FIG. 5 is a schematic representation of multiple sensor configuration further integrating sensor electronics.

Another embodiment is shown in FIG. 5. The now familiar elements, 501-511 of a multiple stack system similar to that shown in FIG. 3, are combined with detection electronics of a photodiode 512 powered by leads 517, and power and signal lines 513, 514, 515 connected from the photo diode to an analog to digital converter 518. The digital signal is connected to the outside signal processing electronics, not shown, through a signal line 520. The signal processing electronics may be on the same substrate 519 or remotely located. Variations on the theme will now be familiar. In another embodiment, not shown, the designs of FIG. 2 and FIG. 5 may be combined. The sensor and excitation elements of the multiple stacks of FIG. 5 are separated as shown in FIG. 2. In another embodiment, the multiple independent interferometers of the design of FIG. 4 are combined with the integrated sensor electronics of FIG. 5. In another embodiment the elements of the embodiments of FIGS. 2, 4 and 5 may be combined to provide on board electronics with separate excitation and detection stacks and multiple independent interferometers.

Figure 6:
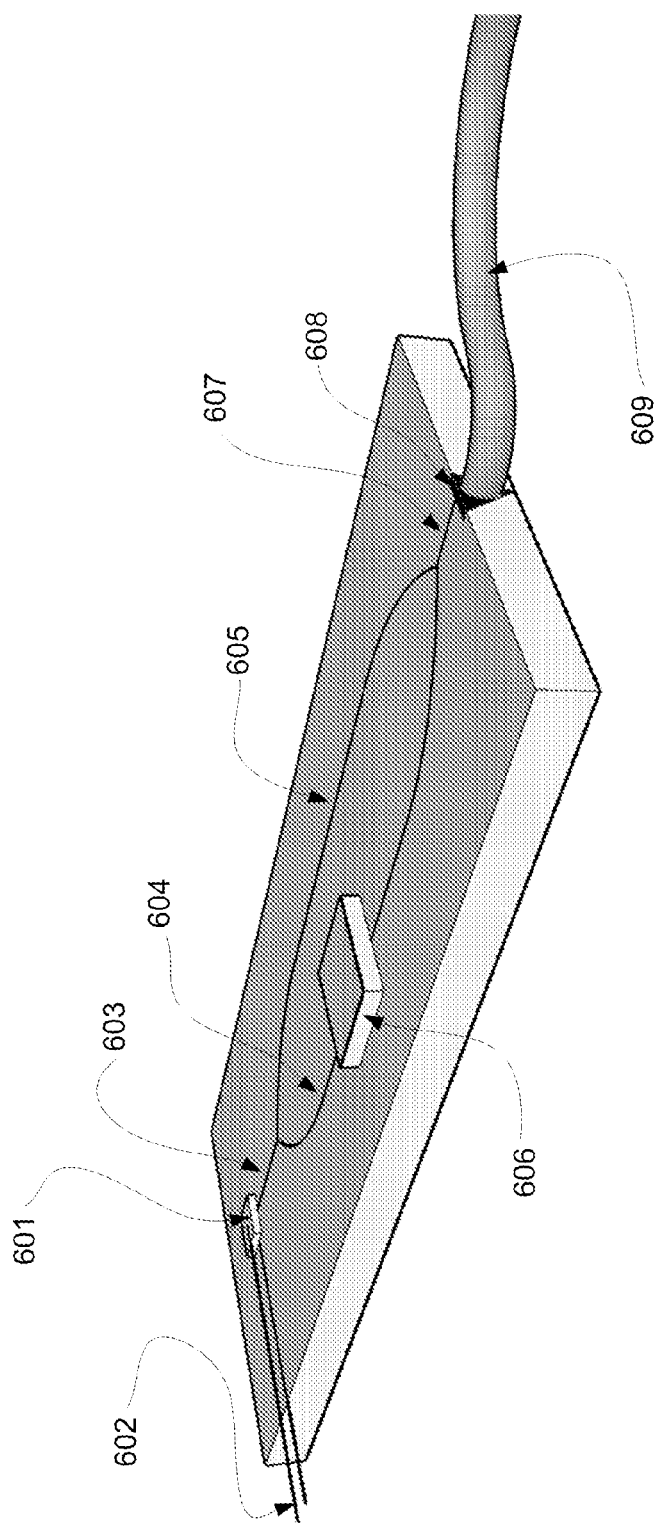
FIG. 6 is a schematic representation of a single element detection device.

In another embodiment of the invention shown in FIG. 6, the sensor is further reduced to a minimum of parts consisting of a laser diode 601 powered through leads 602 attached to a power supply, not shown. The light from the diode is emitted into the light channel 603 and is thereafter split into the two arms of the interferometer 604, 605. A remote acoustical signal to be analyzed is captured by the receiving layer 606, which is positioned over one arm 604 of the interferometer. The acoustical signal impinges on the receiving layer 606 and causes a mechanical stress in relation to the acoustical signal in the one arm 604 of the interferometer. This stress results in a refractive index change and thus a phase shift in the split light signal traveling in the affected arm 604. The light is recombined with the light that has traversed the other arm 605 of the interferometer in the optical channel 607. The optical interference caused by the recombined beams will generate an optical variation related to the absorbed acoustical signal. The light with this "encoded" acoustical signal is connected via a V-groove 608 to an optical fiber 609, which is attached to a photodetector and signal processing circuitry, not shown. In another embodiment, not shown, the device may be constructed such that there are no electrical connections to the sensor. The laser diode of FIG. 6 may be located remotely from the sensor and connected to the sensor substrate through an optical fiber and V-groove similar to that shown for the exit optical signal shown in FIG. 6. In this configuration there are only optical fiber connections to the sensor device. This may be useful in corrosive, high electrical noise or other environments where it may be desirable to isolate the sensor form all electrical connections.

Figure 7:
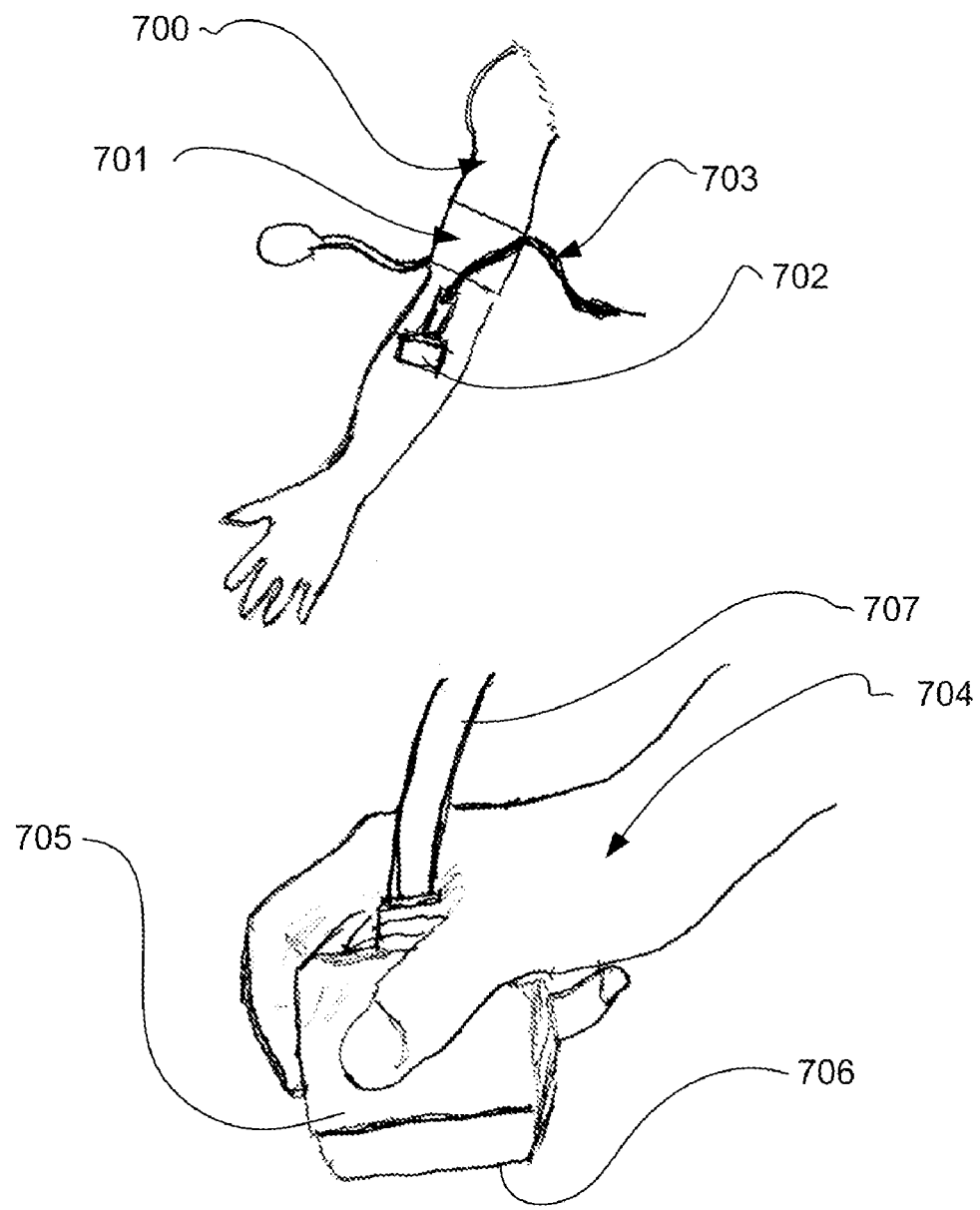
FIG. 7 is a diagram of exemplary physical device configurations.

FIG. 7 shows another exemplary embodiment of the invention with the sensor incorporated into a measurement device that may be used in conjunction with other medical measurement devices. A transducer assembly 702 contains the sensor and excitation electronics previously described in multiple examples of FIGS. 1-6. The optical fiber and electrical connections 703 connect the sensor and excitation elements of the assembly with signal processing electronics, not shown.

Description of the Signals

Signals of relative importance to the functioning of the device are the frequency response of the device with a voltage input acting as an excitation source and the corresponding frequency response of the device as a sensor of the reflected signal detected through the change in the refractive index of the substrate under a strain. These two signals of interest are mathematically modeled using equivalent circuit techniques and a selection of a reasonable set of material properties from standard literature. Both results are discussed below.

Transmit Mode Frequency Response

Figure 8:
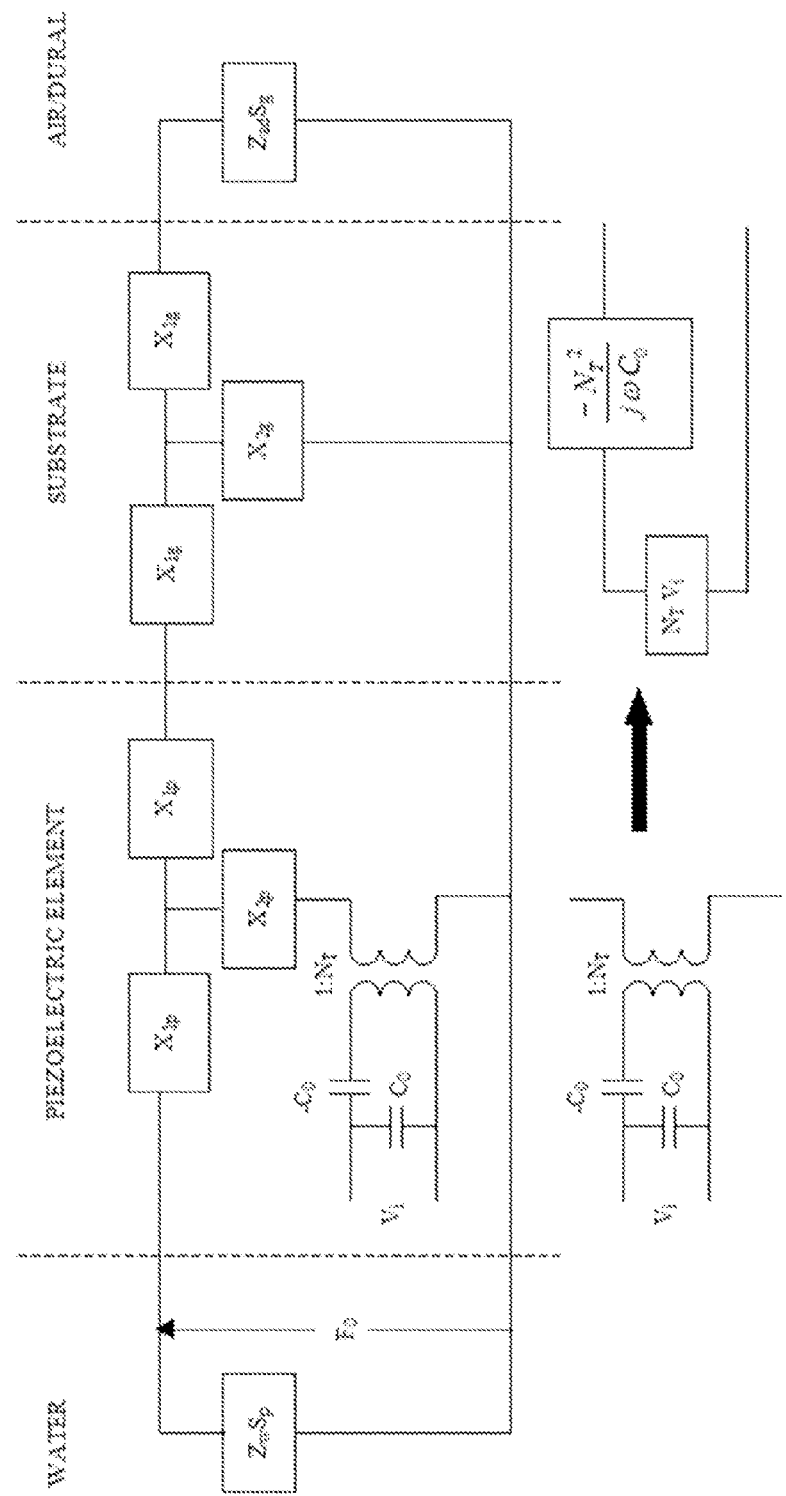
FIG. 8 is an equivalent circuit model for voltage input to pressure output.
Figure 9:
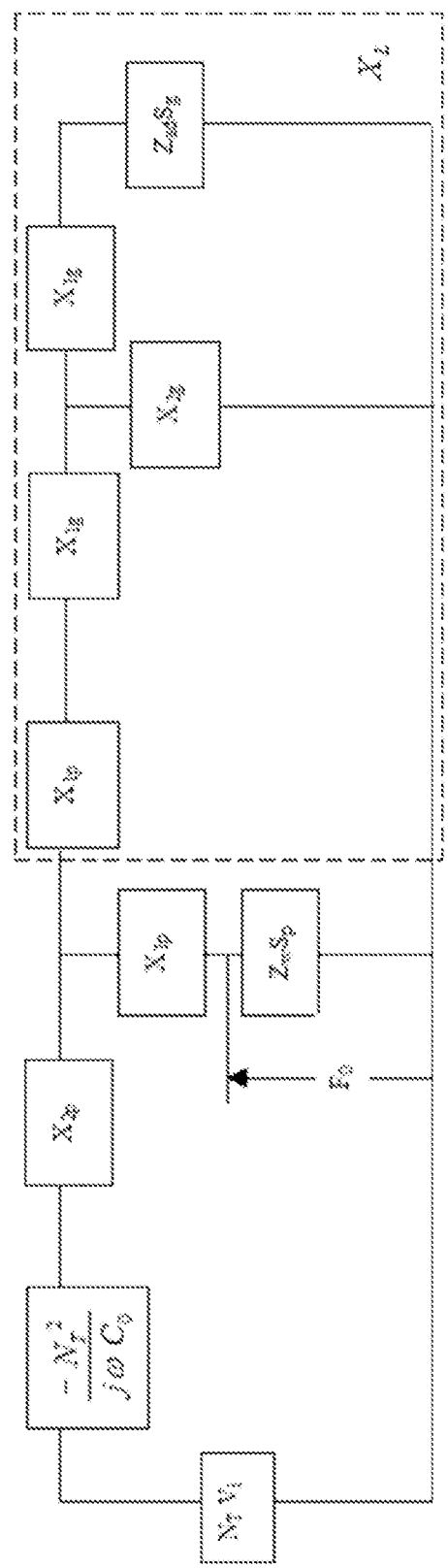
FIG. 9 is an equivalent circuit model of FIG. 8 with substitution of electric components of the piezoelectric elements and rearrangement.
Figure 10:
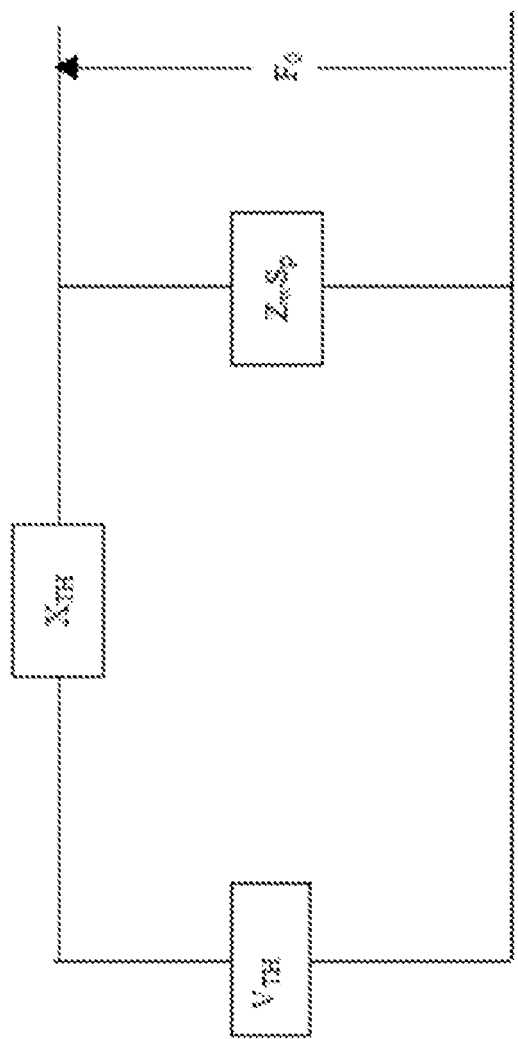
FIG. 10 is the reduced circuit equivalent of FIG. 8.

Modeling techniques may be used to provide a frequency domain, equivalent circuit models. A model using techniques originally devised by Mason (W. P. Mason, Physical Acoustics and the Properties of Solids. D. Van Nostrand Company, Princeton, N.J. 1958) of the single element transducer structure of FIG. 1 follows. The resulting model may then be used to mathematically demonstrate the impulse response and the sensitivity of the single element transducer by calculating the "round trip" of a signal beginning with the electrical excitation signal, the emitted pressure pulse into water, the mechanical excitation of the stack by the perfect reflection of the pressure signal, the mechanical modulation of the interferometer arm, and the resulting optical interferometer output. For demonstrating the sensitivity, it will be simple and sufficient to use a single sinusoid of chosen frequency for the electronic voltage input signal. The equivalent circuit model from which the transfer function may be obtained is shown in FIG. 8 along with the conversion of the electronic components in piezoelectric element model to their frequency domain equivalent components. The model is for a device immersed in water with reflection from a perfectly reflecting sample. The input voltage is labeled Vi and the resulting output pressure is labeled F0. When the electronic components of the piezoelectric element model in the frequency domain are substituted into the model in FIG. 8, and with some rearrangement, the frequency domain circuit equivalent shown in FIG. 9 is obtained. The basic circuit reduction techniques apply to the circuit model in FIG. 9. These Include parallel and series addition and Thevenin's theorem. When these techniques are employed, the reduced circuit in FIG. 10 is obtained. The relevant equations obtained from FIGS. 9 and 10 are given by:

$$X_L = X_{1p} + X_{1g} + \frac{X_{2g}(X_{1g} + Z_{ad}S_g)}{X_{2g} + X_{1g} + Z_{ad}S_g} \quad \text{I}$$

$$V_{TH} = N_T V_i \frac{X_L}{X_1 + X_{2p} - \frac{N_T^2}{j\omega C_0}} \quad \text{II}$$

$$X_{TH} = X_{1p} + \frac{X_L\left(X_{2p} - \frac{N_T^2}{j\omega C_0}\right)}{X_L + X_{2p} - \frac{N_T^2}{j\omega C_0}} \quad \text{III}$$

$$F_0 = V_{TH} \frac{Z_g S_p}{X_{TH} + Z_g S_p} \quad \text{IV}$$

Table 1 displays the parameter value definitions chosen to evaluate the equations I-IV relevant to FIGS. 9 and 10.

TABLE 1

| PARAMETERS | PZT | GLASS | AIR | WATER | Dural |
|---|---|---|---|---|---|
| piezoelectric coefficient (C N$^{-1}$) | $d_{33} = 450\ 10^{-12}$ | — | — | — | — |
| normal elzatic compliance (m$^2$ N$^{-1}$) | $s_{33} = 19\ 10^{-12}$ | — | — | — | — |
| normal dilectric constant (F m$^{-1}$) | $\in_{33} = 2400$ | — | — | — | — |
| electrical loss factor | $\delta_e = \text{ArcTan}[0.015]$ | — | — | — | — |
| mechanical loss factor | $\delta_m = \text{ArcTan}[0.001]$ | — | — | — | — |
| surface area (m$^2$) | $S_p = 1\ 10^{-4}$ | $S_g = 1\ 10^{-4}$ | — | — | — |
| thickness (m) | $t_p = 662\ 10^{-6}$ | $t_g = 662\ 10^{-6}$ | — | — | — |
| density (kg m$^{-3}$) | $\rho_p = 7900$ | $\rho_g = 3000$ | — | — | $\rho_d = 2790$ |
| longitudinal sound velocity (m s$^{-1}$) | $V_p = 3900$ | $V_g = 4500$ | — | — | $V_d = 6319$ |
| acoustic impedance (kg m$^{-2}$ s$^{-1}$) | $Z_p = \rho_p V_p$ | $Z_g = \rho_g V_g$ | $Z_a = 330$ | $Z_w = 1.5\ 10^6$ | $Z_{ad} = \rho_d V_d$ |

The angular frequency is defined by V:

$$\omega = 2\pi f; \qquad \text{V}$$

For the purpose of this example, Dural is chosen as the backing to the substrate. The dural backing is represented by the acoustic impedance Zad on the right-hand side of FIGS. 8 and 9.

$$Z_{ad} = \rho_d V_d \qquad \text{VI}$$

The following set of equations emerge from the modeling theory and represent the frequency domain components of FIGS. 8, 9, and 10.

$$Z_p = \rho_p V_p; \qquad \text{VII}$$

$$Z_g = \rho_g V_g; \qquad \text{VIII}$$

$$C_0 = \frac{\epsilon_{33}(1 - j\text{Tan}[\delta_e])S_p}{t_p}; \qquad \text{IX}$$

$$X_{1p} = jZ_p S_p \text{Tan}\left[\frac{\omega t_p}{2V_p}\right]; \qquad \text{X}$$

$$X_{2p} = \frac{Z_p S_p}{j\text{Sin}\left[\frac{\omega t_p}{V_p}\right]}; \qquad \text{XI}$$

$$N_T = \frac{d_{33} S_p}{t_p(s_{33}(1 + j\text{Tan}[\delta_m]))}; \qquad \text{XII}$$

$$X_{1g} = jZ_g S_g \text{Tan}\left[\frac{\omega t_g}{2V_g}\right]; \qquad \text{XIII}$$

$$X_{2g} = \frac{Z_g S_g}{j\text{Sin}\left[\frac{\omega t_g}{V_g}\right]}; \qquad \text{XIV}$$

Figure 11:
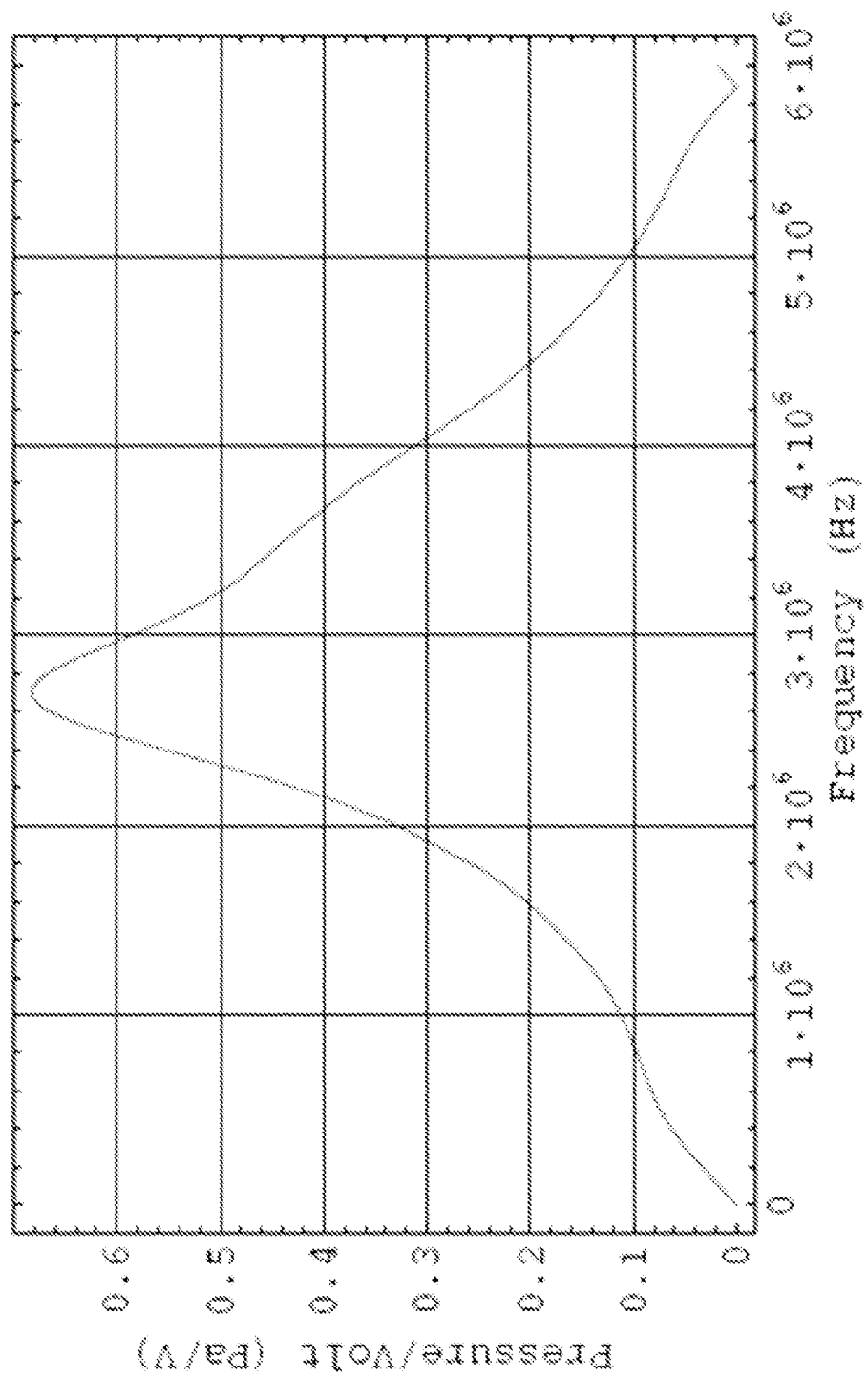
FIG. 11 is a plot of the transfer function for input voltage to output pressure.

The transfer function from input voltage to pressure output XV, is given by XVI, whose plot is shown in FIG. 11. The plot demonstrates the wideband frequency response of the transmit mode of the single element transducer. Due to the modeled transducer structure, the peak of the frequency response occurs at a slightly lower frequency, 2.8 MHz, rather than the expected 3.0 MHz.

$$G_{VP}[f] = F_0/V_b \qquad \text{XV}$$

$$G_{VP}[f_-] = N_T \frac{X_L}{X_L + X_{2p} - \frac{N_T^2}{j\omega C_0}} \frac{Z_w S_p}{Z_w S_p + X_{TH}}; \qquad \text{XVI}$$

Embodiments of the invention provide for custom selection of the frequency peak and breadth based upon the material and design parameters of the analysis shown above.

Receive Mode Frequency Response

Figure 12:
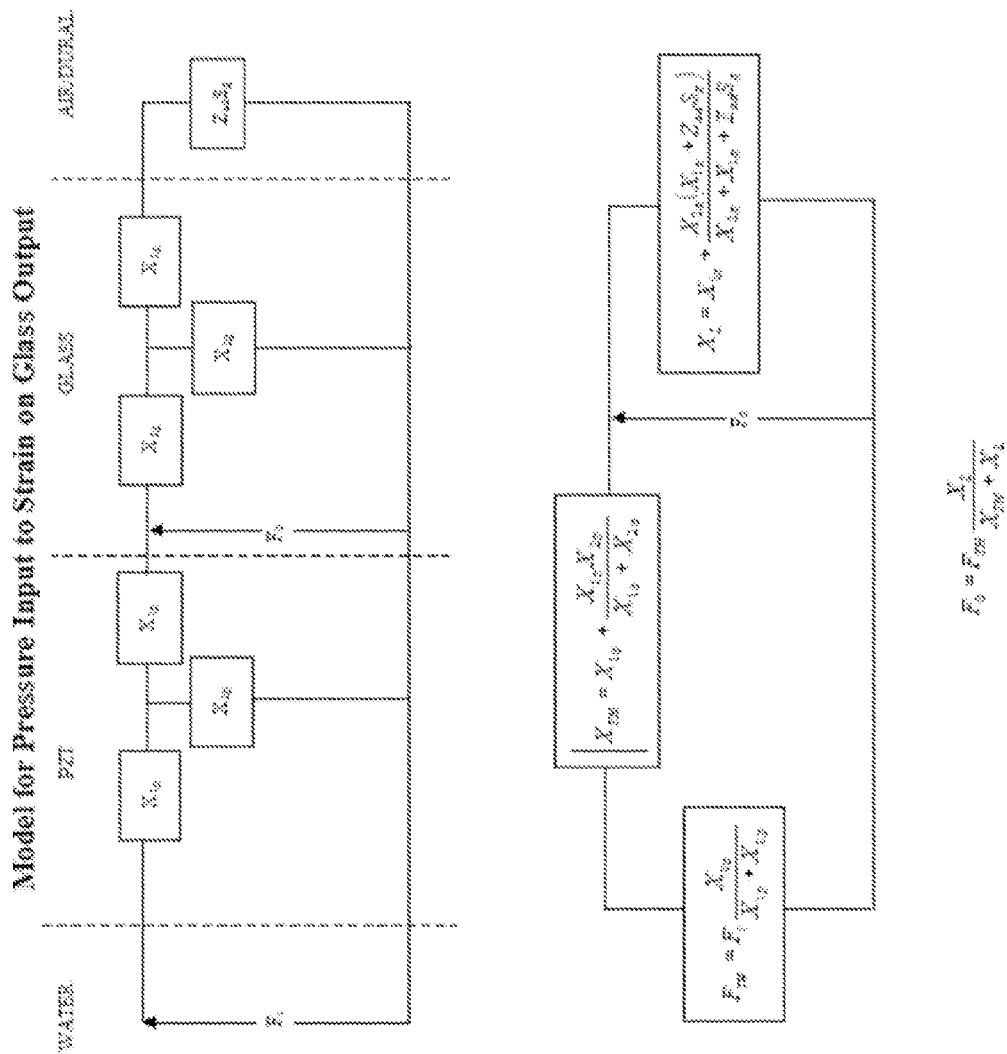
FIG. 12 is a reduced equivalent circuit model for a receiver embodiment.

The frequency response of the transfer function for pressure input to strain on the glass is similarly modeled using equivalent circuit analysis. FIG. 12 shows the reduced equivalent circuit analysis for the receive mode operation of the transducer. The model allows calculation of the strain resulting on the glass substrate induced by the pressure wave of the acoustic signal. The transfer function of pressure input to strain on the glass output XVII is given by equation XVIII.

$$G_{PS}[f] = F_0/F_b \qquad \text{XVII}$$

$$G_{PS}[f_-] = \frac{X_{2p}}{X_{1p} + X_{2p}} \frac{X_L}{X_{TH} + X_L} \qquad \text{XVIII}$$

Figure 13:
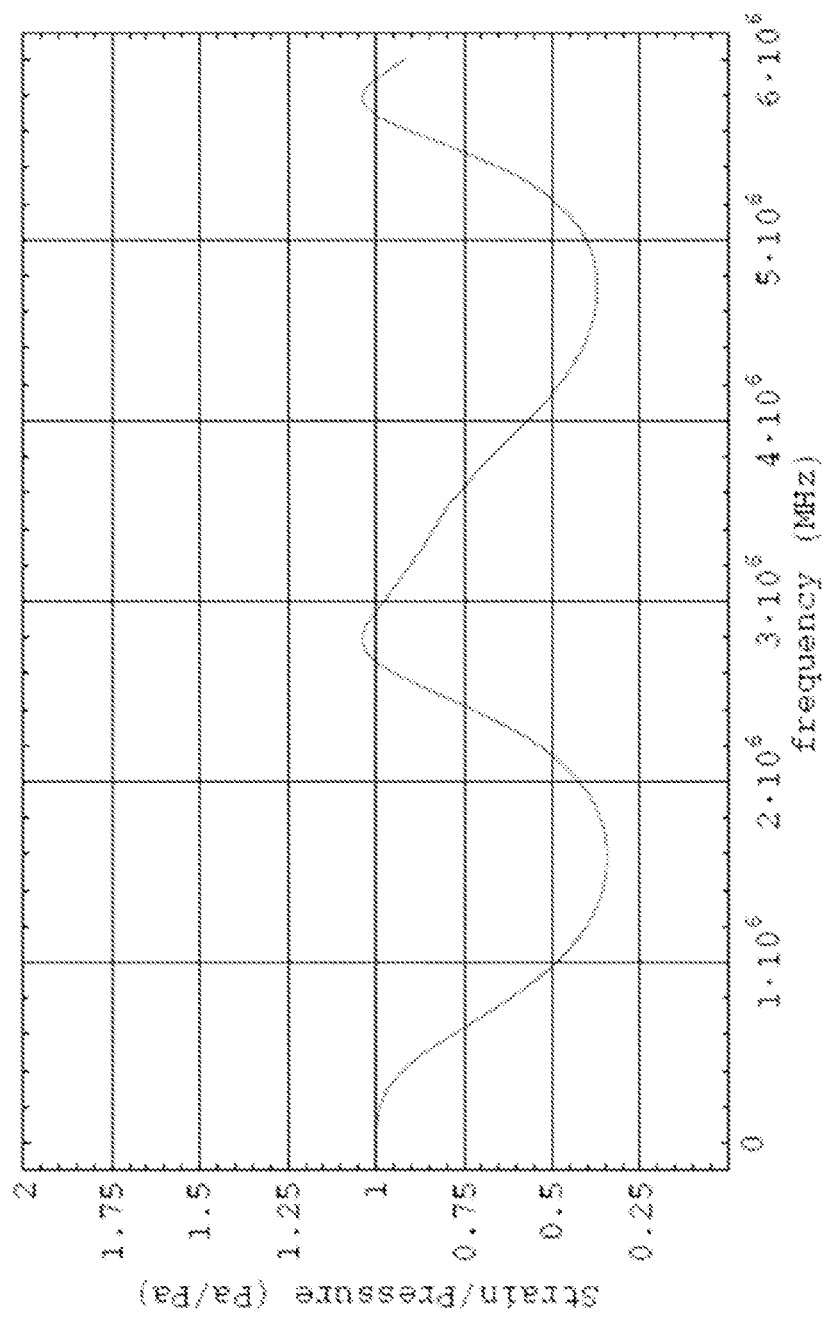
FIG. 13 is a plot of the transfer function for the receiver embodiment of FIG. 12.

Using the same parameter set of Table 1, a plot of the frequency response of the transfer function is shown in FIG. 13. The plots demonstrate that the exemplary single element transducer design has a wideband frequency response in receive mode. Other embodiments of the invention enable customization of the receive mode transfer function frequency response through selection of material and design parameters using the above analysis.

Conversion of Strain on Glass to Optical Intensity and Sensitivity

Ultimately, operation of the device requires that there is sufficient sensitivity to detect the reflected acoustical signal. This sensitivity is related to the transmit and receive mode transfer functions and to the resultant change in refractive index of the substrate resulting from the induced strain. Sensitivity of the device is then demonstrated as follows by showing the resultant change in the optical signal. The change in the index of refraction is given by equation XIX, where n is the index of refraction and p11 is the elasto-optic constant for the substrate material. In an exemplary embodiment, the substrate material is glass, such as Schott® #8350 soda lime glass. From product technical information documents, the refractive index of Schott® #8350 soda lime glass is n=1.514 and the elasto-optic constant is p11=2.6×10−6.

$$\Delta n_0 = \Delta n = \frac{n^3}{2} p_{11} S_{11} \quad \text{XIX}$$

Assuming negligible losses in the transmission and reflection of the acoustical signals through the water medium, the magnitude of the strain on the substrate is given by the magnitude of the transmitted signal into the water medium multiplied by the absolute value of the transfer function from pressure input to strain on the substrate, XX, $$S_{11} = V_i \text{Abs}[G_{VP}[f]] \text{Abs}[G_{PS}[f]] \quad \text{XX}$$

where the magnitude of the transmitted signal into the water medium is given by the product of the voltage input and the absolute value of the transfer function from voltage input to pressure output.

With no modulation and assuming the initial intensity of the interferometer output is unity, the equations describing a Mach-Zehnder interferometer with one arm of the interferometer one-quarter wavelength longer than the other are XXI and XXII:

$$\Delta n_0[f_-, t_-] = \left(\frac{n^3}{2} p_{11}\right) S_{11} \quad \text{XXI}$$

$$\text{INT}[f_-, t_-] = \left(1 + \text{Cos}\left[\frac{2\pi}{\lambda_0} \Delta n_0[f, t] \sqrt{s_P} + \frac{\pi}{2}\right]\right) \quad \text{XXII}$$

A 5 volt input signal at a frequency of 1.5 MHz may be mathematically represented as shown in XXIII, $$f = 1.5 \cdot 10^6; V_i = 5 \text{ Sin}[2\pi ft] \quad \text{XXIII}$$

Figure 14:
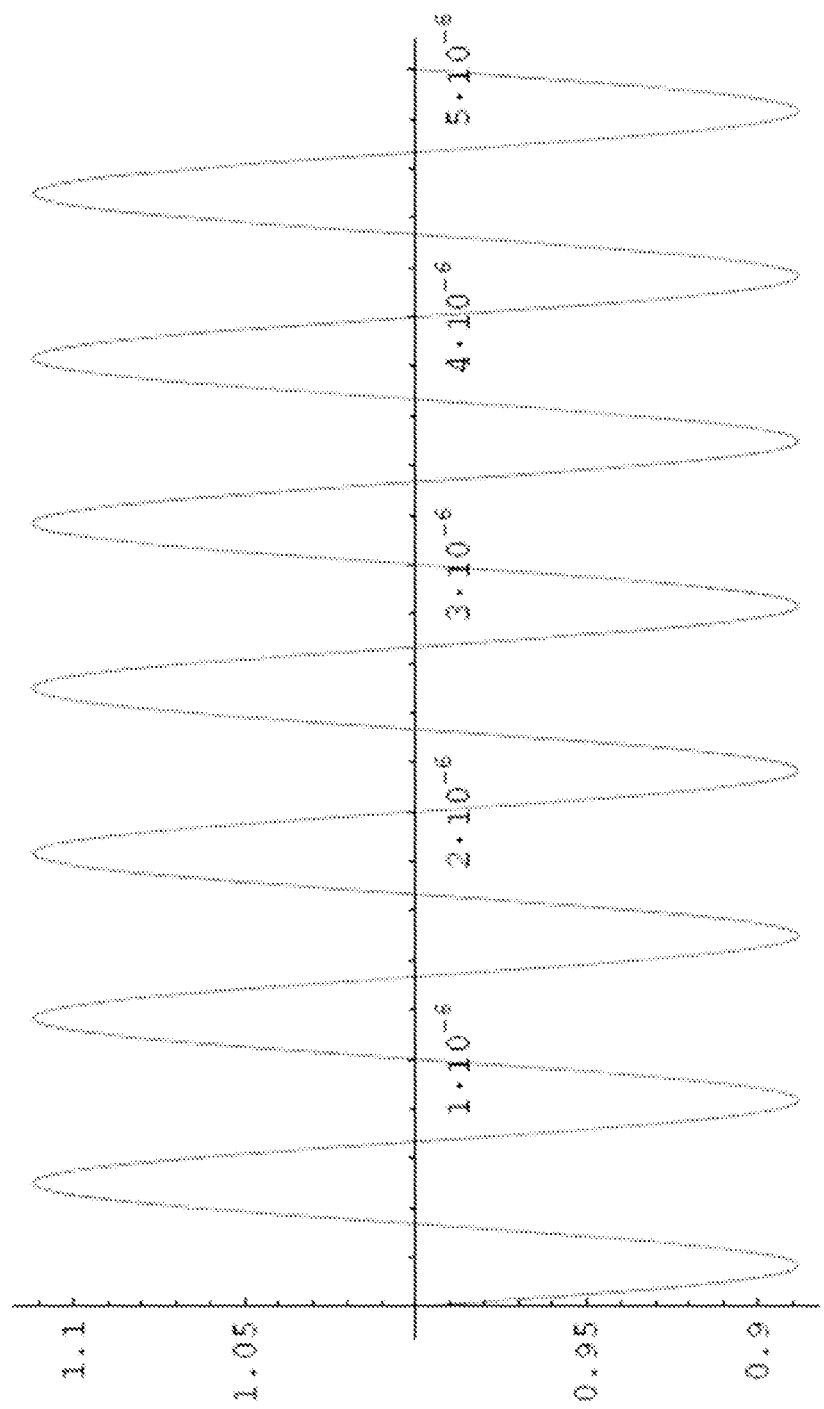
FIG. 14 is a plot of the output intensity of the interferometer.

Assuming a laser diode operating at 0.83 microns, the output optical intensity of the interferometer is as shown in FIG. 14. It is seen that even for a low amplitude voltage input signal of 5 V with a frequency of 1.5 MHz that corresponds to the minimum receiver mode frequency response as shown in FIG. 13, the intensity of the interferometer output changes 10% about the initially unmodulated output. This level of intensity change is large enough to be easily discernible by standard photodetectors. The single element transducer of this exemplary design has sufficient sensitivity and appropriate frequency response characteristics to operate in a pulsed mode.

Continuous Wave Doppler Transducer

Figure 15:
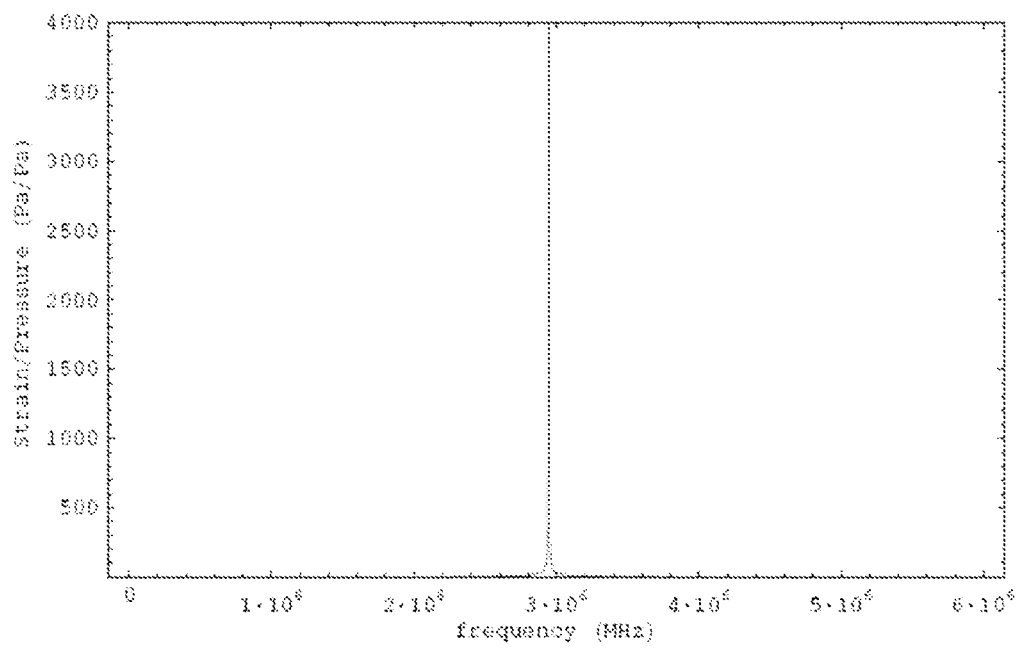
FIG. 15 is a plot of the frequency response of the receive mode for an embodiment of the invention.
Figure 15:
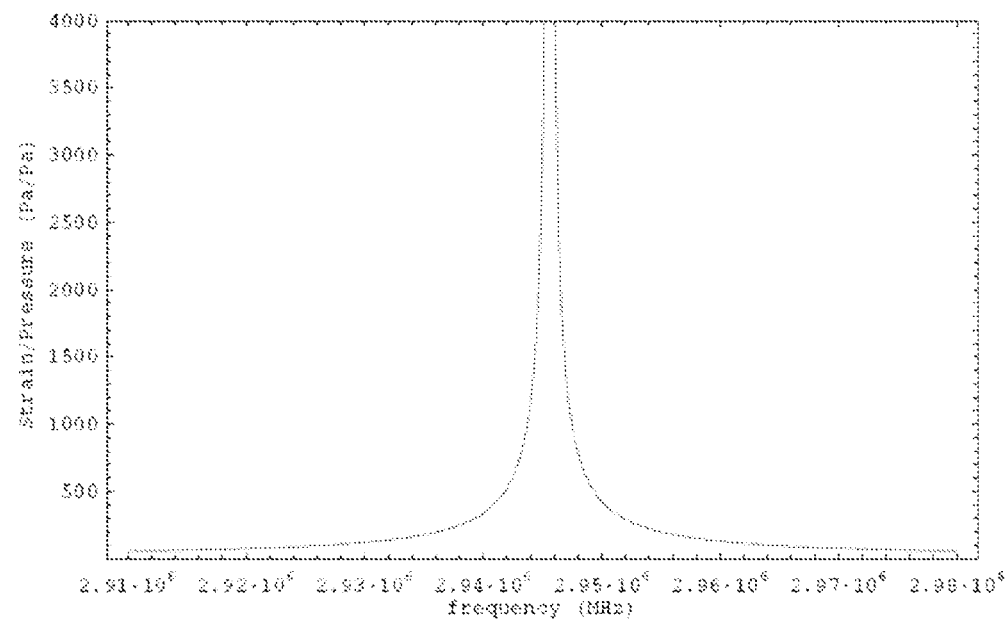

In another embodiment described as an example in FIG. 2 above, continuous excitation of the sample to be analyzed is enabled. The frequency response characteristics and the sensitivity of this type embodiment are now provided. For simplification of the analysis, the matching layer 203 of the excitation stack 203-206 is neglected. If the transducer is chosen to operate at 3 MHz, and the material characteristic parameters of the previous exemplary analysis are selected, Table 1, the results for the transmitted stack frequency response is the same as previously calculated and shown in FIG. 11. The resonant frequency of the receiving stack is tuned through selection of the thickness and material of the receiving stack layer 202. If the layer 202 is made of the same piezoelectric material as used in the previous example and whose parameters are given in Table 1, the thickness of the layer 202 would be ½ of that for the previous example or 331 microns. The analysis for the frequency response of the receiving mode is the same as the previous example. The frequency response XVI with the configuration is now changed from the previous example through selection of the thickness of the layer 202 is shown in FIG. 15. The upper graph shows that there is a single mechanical resonance at 3 MHz. The lower graph is a scale expansion of the upper graph showing a narrow resonant receiver transfer function frequency response.

Figure 16:
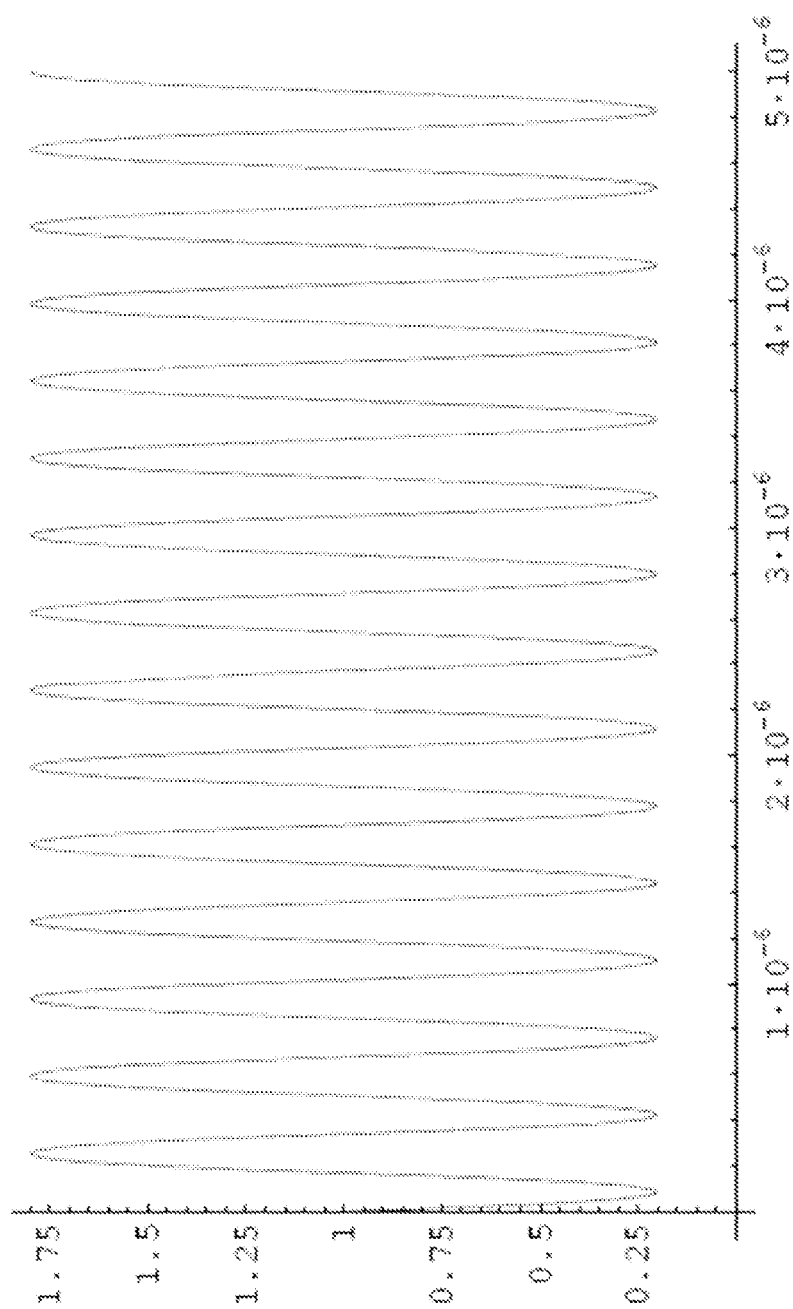
FIG. 16 is a plot of the output intensity of the interferometer for a continuous mode embodiment of the invention.

Conversion of Strain on Glass to Optical Intensity and Sensitivity for Continuous Wave Transducer The calculation of the received signal intensity follows much the same analysis as before. The magnitude of the strain on the glass is given by equation XIX and the equations describing the output of a Mach-Zehnder interferometer are given by previously discussed equations XXI and XXII. The parameters chosen for this example are similar to previous sets, a soda lime glass with refractive index n=1.514 and stress-optical coefficient of p11=2.7×10⁻⁶, operating at 3 MHz and an input voltage to the excitation of just 10 millivolts produces the optical output of FIG. 16. The results indicate that operating at the resonant frequency of the mechanical design, the intensity of the interferometer output changes +/−75% about the initial output intensity. The intensity change is sufficient to be easily detected by a standard photodetector. The design of the present invention has appropriate frequency response characteristics and sensitivity to operate in a continuous mode.

Particular embodiments of the invention for the frequency response characteristics and the sensitivity analysis included a glass substrate and an operating frequency as is commonly used in the technology. These embodiments are however exemplary only. Variations in the materials and geometries should now be obvious to those skilled in the art. Embodiments of the invention provide a means to select appropriate materials, geometries and other operating parameters discussed here to produce a customized transducer for particular ultrasonic analysis applications. The mathematical models discussed above focused on the particular embodiments of a single transducer operating in a pulsed mode and a single transducer operating in a continuous mode, as are for example depicted in FIGS. 1 and 2 respectively. It will be clear to those skilled in the art that analogous analysis and design options apply to the other embodiments discussed.

CONCLUSIONS

A new optical ultrasonic analysis transducer is described. The device includes a new detection means for the reflected ultrasound signal. The detector may be incorporated into a microchip design. The detector is compatible with a variety of material and design geometries that may be optimized for the particular application. Versions of the device may optionally include both excitation and receiving elements on the same device or these elements may be separate. Example designs are shown with applications to continuous wave ultrasound analysis useful for example in Doppler fluid flow measurements. Other designs are shown with multiple arrays and multiple excitation transducers to allow flexible three-dimensional imaging apparatus to be built. An equivalent circuit analysis of the frequency response and signal sensitivity provides means to customize material selection and other design parameters for particular applications.

I claim:

1. An ultrasound analysis device comprising:
   a) a substrate with a top and bottom surface,
   b) a Mach-Zehnder interferometer, comprised of an input wave-guide, two optical channel wave-guides, and an exit wave-guide, formed on the top surface of the substrate wherein one of the two optical channel wave-guides that form the interferometer is longer than the other optical channel wave-guide that forms the interferometer by a length equivalent to one-quarter wavelength of the output wavelength of the laser diode,
   c) an acoustic signal receiving element located over one of the arms of the interferometer, and
   d) a laser diode having a characteristic output wavelength attached to the top surface of the substrate, an optical wave-guide formed in the substrate connecting the output of the laser diode to the input of the interferometer and an optical wave-guide connecting the exit of the interferometer to an optical fiber.

2. An ultrasound analysis device comprising:
   a) a substrate with a top and bottom surface,
   b) a Mach-Zehnder interferometer, comprised of an input wave-guide, two optical channel wave-guides, and an exit wave-guide, formed on the top surface of the substrate,
   c) an acoustic signal receiving element located over one of the arms of the interferometer, and
   d) a piezoelectric excitation device having a characteristic operating frequency range.

3. The device of claim 2 wherein the acoustic signal receiving element is designed so as to have a mechanical resonance within the characteristic operating frequency range of the piezoelectric excitation device.

4. An ultrasound analysis device comprising:
   a) a substrate with a top and a bottom surface,
   b) a Mach-Zehnder interferometer, comprised of an input wave-guide, two optical channel wave-guides, and an exit wave-guide, formed on the top surface of the substrate, and
   c) a transducer stack comprised of the elements of a backing layer attached to the top surface of the substrate over the top of one of the optical channel wave-guides of the interferometer, an electrode for activating a piezoelectric device positioned on top of the backing layer, a piezoelectric crystal positioned on top of the electrode, a second electrode for activating a piezoelectric device positioned on top of the piezoelectric crystal and a matching layer located on top of the second electrode, and
   d) a laser diode having a characteristic output wavelength attached to the top surface of the substrate, an optical wave-guide formed in the substrate connecting the output of the laser diode to the input of the interferometer and an optical wave-guide connecting the exit of the interferometer to an optical fiber.

5. The device of claim 4 wherein one of the two optical channel wave-guides that form the interferometer is longer than the other optical channel wave-guide that forms the interferometer by a length equivalent to one-quarter wavelength of the output wavelength of the laser diode.

6. The device of claim 4 wherein the substrate is made of glass.

7. The device of claim 4 wherein the substrate material is selected from one of: $SiO_xN_y/SiO2/Si$, $TiO_2/SiO_2/Si$, Lithium Niobate, InP, GaAs, polyethylene terephthalate, polyethylene naphthalate, and poly(4,4'-oxydiphenylene-pyromellitimide).

8. The device of claim 4 further comprising at least one additional transducer stack positioned separately but on the same optical channel wave-guides of the interferometer.

9. An ultrasound analysis device comprising:
   a) a substrate with a top and a bottom surface,
   b) a Mach-Zehnder interferometer, comprised of an input wave-guide, two optical channel wave-guides, and an exit wave-guide, formed on the top surface of the substrate, and
   c) an excitation transducer stack comprised of the elements of a backing layer attached to the top surface of the substrate and not over the top of either of the optical channel wave-guides of the interferometer, an electrode for activating a piezoelectric device positioned on top of the backing layer, a piezoelectric crystal having a characteristic operating frequency range positioned on top of the electrode, a second electrode for activating a piezoelectric device positioned on top of the piezoelectric crystal and a matching layer located on top of the second electrode, and
   d) an acoustic signal receiving element located over one of the arms of the interferometer, and
   e) a laser diode having a characteristic output wavelength attached to the top surface of the substrate, an optical wave-guide formed in the substrate connecting the output of the laser diode to the input of the interferometer and an optical wave-guide connecting the exit of the interferometer to an optical fiber.

10. The device of claim 9 wherein one of the two optical channel wave-guides that form the interferometer is longer than the other optical channel wave-guide that forms the interferometer by a length equivalent to one-quarter wavelength of the output wavelength of the laser diode.

11. The device of claim 9 wherein the substrate is made of glass.

12. The device of claim 9 wherein the substrate material is selected from one of: $SiO_xN_y/SiO2/Si$, $TiO_2/SiO_2/Si$, Lithium Niobate, InP, GaAs, polyethylene terephthalate, polyethylene naphthalate, and poly(4,4'-oxydiphenylene-pyromellitimide).

13. The device of claim 9 further comprising at least one additional excitation transducer stack and at least one additional acoustic signal receiving element.

14. The device of claim 9 wherein the acoustic signal receiving element is designed so as to have a mechanical resonance within the characteristic operating frequency range of the piezoelectric element.

15. The device of claim 13 wherein each of the acoustic signal receiving elements is designed so as to have a mechanical resonance within the characteristic operating frequency range of at least one of the piezoelectric elements.

16. An ultrasound analysis device comprising:
   a) a substrate with a top and a bottom surface,
   b) a plurality of Mach-Zehnder interferometers, each comprised of an input wave-guide, two optical channel wave-guides, and an exit wave-guide, formed on the top surface of the substrate, and
   c) a plurality transducer stacks equal in number to the number of interferometers, each comprised of the elements of a backing layer attached to the top surface of the substrate over the top of one of the optical channel wave-guides of one of the interferometers, an electrode for activating a piezoelectric device positioned on top of the backing layer, a piezoelectric crystal positioned on top of the electrode, a second electrode for activating a piezoelectric device positioned on top of the piezoelectric crystal and a matching layer located on top of the second electrode, and d) a plurality of laser diodes equal in number to the number of interferometers attached to the top surface of the substrate, and each having a characteristic output wavelength, an optical wave-guide formed in the substrate connecting the output of the laser diode to the input of one of the interferometers and an optical wave-guide connecting the exit of the one of the interferometers to an optical fiber.

17. The device of claim 16 wherein one of the two optical channel wave-guides that form each of the interferometers is longer than the other optical channel of the wave-guide that forms the same interferometer by a length equivalent to one-quarter wavelength of the output wavelength of the laser diode attached to that interferometer.

18. The device of claim 16 wherein the substrate is made of glass.

19. The device of claim 16 wherein the substrate material is selected from one of: $SiO_xN_y/SiO2/Si$, $TiO_2/SiO_2/Si$, Lithium Niobate, InP, GaAs, polyethylene terephthalate, polyethylene naphthalate, and poly(4,4'-oxydiphenylene-pyromellitimide).

* * * * *